United States Patent [19]

Krämer et al.

[11] Patent Number: 4,845,098
[45] Date of Patent: Jul. 4, 1989

[54] SACCHARINE SALTS OF SUBSTITUTED HYDROXYPROPYLAMINES, COMPOSITIONS AND USE

[75] Inventors: Wolfgang Krämer, Burscheid; Joachim Weissmüller, Monheim; Paul Reinecke; Gerd Hänssler, both of Leverkusen, all of Fed. Rep. of Germany

[73] Assignee: Bayer Aktiengesellschaft, Leverkusen, Fed. Rep. of Germany

[21] Appl. No.: 118,144

[22] Filed: Nov. 5, 1987

[30] Foreign Application Priority Data

Nov. 22, 1986 [DE] Fed. Rep. of Germany ....... 3639902

[51] Int. Cl.$^4$ .................... A01N 43/84; C07D 413/02
[52] U.S. Cl. .................. 514/238.8; 514/212; 514/253; 514/321; 514/373; 514/239.2; 540/609; 544/135; 544/368; 546/198; 548/211
[58] Field of Search ............... 540/609; 544/135, 368; 546/198; 548/211; 514/212, 231, 253, 321, 373, 239.5

[56] References Cited

FOREIGN PATENT DOCUMENTS 0129321 12/1984 European Pat. Off. .
0158074 10/1985 European Pat. Off. .

Primary Examiner—Robert W. Ramsuer
Attorney, Agent, or Firm—Sprung Horn Kramer & Woods

[57] ABSTRACT

Fungicidal saccharine salts of substituted hydroxypropylamines of the formula

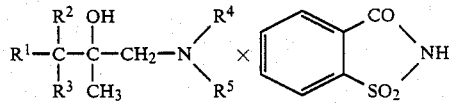

in which
$R^1$ is optionally substituted phenyl, phenoxy, phenylthio, phenylalkyl, phenoxyalkyl, or phenylthioalkyl, or optionally substituted cyclohexyl, cyclohexyloxy, cyclohexylalkyl, cyclohexyloxyalkyl or cyclohexylthioalkyl,
$R^2$ is hydrogen or methyl,
$R^3$ is methyl or ethyl, and
$R^4$ and $R^5$ each independently is alkyl or alkenyl, or
$R^4$ and $R^5$, together with the nitrogen atom to which they are bonded, are an optionally substituted saturated heterocyclic radical which can optionally contain further hetero atoms.

6 Claims, No Drawings

SACCHARINE SALTS OF SUBSTITUTED HYDROXYPROPYLAMINES, COMPOSITIONS AND USE

The present invention relates to new saccharine salts of substituted hydroxypropylamines, a process for their preparation and their use as agents for combating pests.

It is already known that saccharine salts of substituted amines, such as, for example, the saccharine salt of 5-amino-1,2,4-triazole or the saccharine salt of cyclohexylamine, have fungicidal properties (compare European Pat. No. 158,074).

It is furthermore known that certain substituted hydroxyalkylamines, such as, for example, 4-(4-t-butylphenyl)-3-methyl-1-(3-methyl-piperidin-1-yl)-butan-2-ol, have fungicidal properties (compare European Pat. No. 129,321).

However, the activity of these already known compounds is not always completely satisfactory in all fields of use, especially when low amounts are applied and in the case of low concentrations.

New saccharine salts of substituted hydroxypropylamines of the general formula (I)

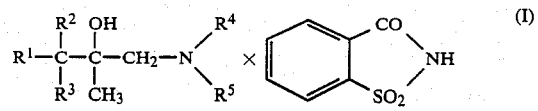

in which
R¹ represents in each case optionally substituted phenyl, phenoxy, phenylthio, phenylalkyl, phenoxyalkyl or phenylthioalkyl, or represents in each case optionally substituted cyclohexyl, cyclohexyloxy, cyclohexylthio, cyclohexylalkyl, cyclohexyloxyalkyl or cyclohexylthioalkyl,
R² represents hydrogen or methyl,
R³ represents methyl or ethyl and
R⁴ and R⁵ independently of one another represent alkyl or alkenyl, or
R⁴ and R⁵, together with the nitrogen atom to which they are bonded, represent an optionally substituted saturated heterocyclic radical, which can optionally contain further hetero atoms,
have been found.

The compounds of the formula (I) can be obtained as geometric and/or optical isomers or isomer mixtures of varying composition. Both the pure isomers and the isomer mixtures are claimed according to the invention.

It has furthermore been found that the new saccharine salts of substituted hydroxypropylamines of the general formula (I)

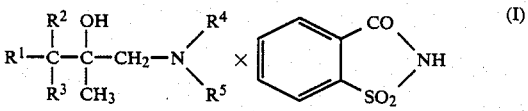

in which
R¹ represents in each case optionally substituted phenyl, phenoxy, phenylthio, phenylalkyl, phenoxyalkyl or phenylthioalkyl, or represents in each case optionally substituted cyclohexyl, cyclohexyloxy, cyclohexylthio, cyclohexylalkyl, cyclohexyloxyalkyl or cyclohexylthioalkyl,
R² represents hydrogen or methyl,
R³ represents methyl or ethyl and
R⁴ and R⁵ independently of one another represent alkyl or alkenyl, or
R⁴ and R⁵, together with the nitrogen atom to which they are bonded, represent an optionally substituted saturated heterocyclic radical, which can optionally contain further hetero atoms,
are obtained by a process in which substituted hydroxypropylamines of the formula (II)

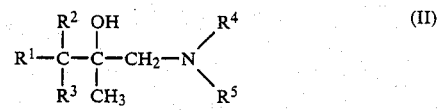

in which
R¹, R², R³, R⁴ and R⁵ have the abovementioned meaning,
are reacted with saccharine, if appropriate in the presence of a diluent.

Finally, it has been found that the new saccharine salts of substituted hydroxypropylamines of the general formula (I) have an action against pests.

Surprisingly, the saccharine salts of substituted hydroxypropylamines of the general formula (I) according to the invention inter alia have a better fungicidal activity than the substituted amine saccharine salts which are known from the prior art, such as, for example, the saccharine salt of 5-amino-1,2,4-triazole or the saccharine salt of cyclohexylamine, and likewise have a considerably better fungicidal activity than the substituted hydroxyalkylamines known from the prior art, such as, for example, 4-(4-t-butylphenyl)-3-methyl-1-(3-methyl-piperidin-1-yl)-butan-2-ol, which are closely related compounds chemically and from the point of view of their action.

Formula (I) provides a general definition of the saccharine salts of substituted hydroxypropylamines according to the invention. Preferred compounds of the formula (I) are those
in which
R¹ represents phenyl, phenoxy, phenylthio, phenylalkyl, phenoxyalkyl or phenylthioalkyl with in each case 1 or 2 carbon atoms in the alkyl part and in each case optionally mono-, di-, tri-, tetra- or pentasubstituted by identical or different substituents, possible substituents on the phenyl in each case being: halogen, in each case straight-chain or branched alkyl, alkoxy and alkylthio with in each case 1 to 5 carbon atoms and halogenoalkyl, halogenoalkoxy and halogenoalkylthio with in each case 1 or 2 carbon atoms and 1 to 5 identical or different halogen atoms, such as, preferably, fluorine or chlorine atoms; or represents cyclohexyl, cyclohexyloxy, cyclohexylthio, cyclohexylalkyl, cyclohexyloxyalkyl or cyclohexylthioalkyl with in each case 1 or 2 carbon atoms in the alkyl part and in each case optionally monosubstituted or polysubstituted by identical or different substituents, possible substituents on the cyclohexyl in each case being: in each case straight-chain or branched alkyl and alkoxy with in each case 1 to 5 carbon atoms, trifluoromethyl and trifluoromethoxy,
R² represents hydrogen or methyl,
R³ represents methyl or ethyl and R⁴ and R⁵ independently of one another represent straight-chain or branched alkyl with 1 to 8 carbon atoms, or represent straight-chain or branched alkenyl with 3 to 6 carbon atoms, or R⁴ and R⁵, together with the nitrogen atom to which they are bonded, represent a 5- to 7-membered saturated heterocyclic radical which has 1 or 2 hetero atoms, preferably nitrogen or oxygen, and is optionally mono-, di-, tri-, tetra-, penta-, hexa-, hepta-, octa-, nona- or decasubstituted by identical or different substituents, possible substituents being: methyl, ethyl and hydroxymethyl.

Particularly preferred compounds of the general formula (I) are those
in which

R¹ represents phenyl, phenylmethyl, phenoxymethyl, phenylthiomethyl, phenoxy or phenylthio, in each case optionally mono-, di- or trisubstituted by identical or different substituents, possible substituents on the phenyl in each case being: fluorine, chlorine, bromine, methyl, ethyl, n-propyl, i-propyl, n-, i-, s- or t-butyl, n-pentyl, 2-methyl-2-butyl, methoxy, ethoxy, n- or i-propoxy, t-butoxy, trifluoromethyl, trifluoromethoxy and trifluoromethylthio; or represents cyclohexyl, cyclohexylmethyl, cyclohexyloxymethyl, cyclohexylthiomethyl, cyclohexyloxy or cyclohexylthio, in each case optionally mono-, di- or trisubstituted by identical or different substituents, possible substituents on the cyclohexyl in each case being: methyl, ethyl, n- or i-propyl, n-, i-, s- or t-butyl, n-pentyl, 2-methyl-2-butyl, methoxy, ethoxy, n- or i-propoxy, t-butoxy, trifluoromethyl and trifluoromethoxy, R² represents hydrogen or methyl, R³ represents methyl or ethyl and R⁴ and R⁵ independently of one another represent methyl, ethyl, n- or i-propyl, n-, i-, s- or t-butyl, n-pentyl, allyl, 2-butenyl or 3-methyl-2-butenyl, or R⁴ and R⁵, together with the nitrogen atom to which they are bonded, represent 1-pyrrolidinyl, 1-piperidinyl, 1-piperazinyl, 4-morpholinyl or 1-hexahydroazepinyl, in each optionally case mono-, di- or trisubstituted by identical or different substituents from the group comprising methyl, ethyl and hydroxymethyl.

Especially preferred compounds of the general formula (I) are those
in which

R¹ represents phenyl, phenoxy, phenoxymethyl, phenylthiomethyl, phenylthio, cyclohexyloxy, cyclohexylmethyl or cyclohexyloxymethyl, in each case optionally mono- or disubstituted by identical or different substituents from the group comprising chlorine, methyl, t-butyl and tri-fluoromethoxy, R² represents hydrogen or methyl, R³ represents methyl and R⁴ and R⁵, together with the nitrogen atom on which they are located, represent 1-piperidinyl, 4-morpholinyl or 1-hexahydroazepinyl, optionally mono-, di- or trisubstituted by methyl.

The following compounds of the general formula (I) may be mentioned specifically, in addition to the compounds mentioned in the preparation examples:

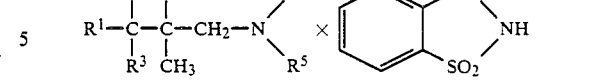

TABLE 1

| R¹ | R² | R³ | -N⟨R⁴/R⁵ |
|---|---|---|---|
| Ph-S-CH₂- | CH₃ | CH₃ | -N(morpholinyl) |
| Ph- | CH₃ | CH₃ | -N(3-methylpiperidinyl) |
| 3-CH₃-C₆H₄-O- | CH₃ | CH₃ | -N(3,5-dimethylpiperidinyl) |
| 4-Cl-C₆H₄-S- | CH₃ | CH₃ | -N(piperidinyl) |
| Ph-O-CH₂- | CH₃ | CH₃ | -N(2,6-dimethylmorpholinyl) |
| Cyclohexyl-O-CH₂- | CH₃ | CH₃ | -N(2,6-dimethylmorpholinyl) |
| Cyclohexyl-CH₂- | CH₃ | CH₃ | -N(3-methylpiperidinyl) |
| 3-CH₃-cyclohexyl-O- | CH₃ | CH₃ | -N(3-methylpiperidinyl) |

TABLE 1-continued

| R¹ | R² | R³ | -N(R⁴)(R⁵) |
|---|---|---|---|
| 3-methylcyclohexyl-CH₂- | H | CH₃ | 2,6-dimethylmorpholin-4-yl |
| 4-tert-butylcyclohexyl-CH₂- | H | CH₃ | piperidin-1-yl |
| 4-trifluoromethoxycyclohexyl-CH₂- | CH₃ | CH₃ | 3,5-dimethylpiperidin-1-yl |
| 3-methylcyclohexyl-O-CH₂- | CH₃ | CH₃ | piperidin-1-yl |

If, for example, 2,3,3-trimethyl-4-(3-methylphenyl)-1-(morpholin-4-yl)-2-butanol is used as the starting compound, the course of the reaction in the process according to the invention can be represented by the following equation:

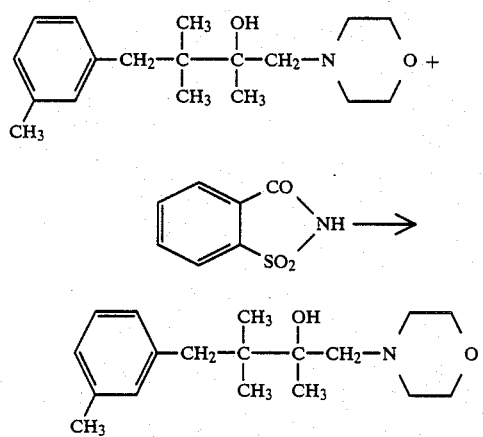

Formula (II) provides a general definition of the substituted hydroxypropylamines required as starting substances for carrying out the process according to the invention. In this formula (II), $R^1$, $R^2$, $R^3$, $R^4$ and $R^5$ represent those radicals which have already been mentioned for these substituents in connection with the description of the substances of the formula (I) according to the invention.

The substituted hydroxypropylamines are known in some cases (compare DE-OS (German Published Specification) 2,505,423). Some of them are the subject of German patent application P 3 627 071 of Aug. 9, 1986, corresponding to U.S. application Ser. No. 079,723, filed July 30, 1987, now pending.

They are obtained, for example, by a process in which epoxides of the formula (III)

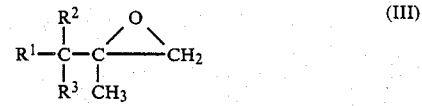

in which $R^1$, $R^2$ and $R^3$ have the abovementioned meaning, are reacted with amines of the general formula (IV)

in which $R^4$ and $R^5$ have the abovementioned meaning, if appropriate in the presence of a diluent, such as, for example, n-butanol, and if appropriate in the presence of a catalyst, such as, for example, acetic acid, at temperatures between 40° C. and 200° C., and, if appropriate, in a 2nd stage, the substituted hydroxypropylamines thus obtainable, of the formula (IIa)

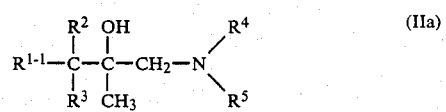

in which $R^{1\text{-}1}$ represents in each case optionally substituted phenyl, phenoxy, phenylalkyl or phenoxyalkyl and $R^2$, $R^3$, $R^4$ and $R^5$ have the abovementioned meaning, are then hydrogenated in the phenyl ring in the customary manner with molecular hydrogen, if appropriate in the presence of a diluent, such as, for example, isopropanol, and if appropriate in the presence of a catalyst, such as, for example, ruthenium-on-carbon, at temperatures between 80° C. and 200° C.

The epoxides of the formula (III) are known (compare, for example, U.S. Pat. No. 4,615,725) or they can be obtained in a generally known manner, for example by a process in which methyl ketones of the formula (V)

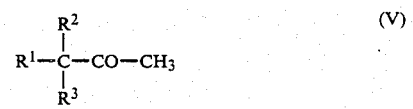

in which $R^1$, $R^2$ and $R^3$ have the abovementioned meaning, are reacted either (α) with dimethyloxosulphonium methylide of the formula (VI)

in a manner in which is known per se in the presence of a diluent, such as, for example, dimethylsulphoxide, at temperatures between 20° C. and 80° C. (in this context, compare the information in J. Am. Soc. 87, 1363–1364 [1965], or (β) with trimethylsulphonium methyl-sulphate of the formula (VII)

in a manner which is known per se in the presence of an inert organic solvent, such as, for example, acetonitrile, and in the presence of a base, such as, for example, sodium methylate, at temperatures between 0° C. and 60° C., preferably at room temperature (compare also the information in Heterocycles 8, 397 [1977]).

The methyl ketones of the formula (V) are known (compare, for example, U.S. Pat. No. 4,549,900 and DE-OS (German Published Specification) 32 10,725), or they can be obtained in an analogous manner by the process described therein.

The epoxides of the formula (III) can also be obtained by a process in which corresponding olefin are epoxidized by processes which are known in principle, for example by reaction with hydrogen peroxide or with peracids.

The amines of the formula (IV) are generally known compounds of organic chemistry.

Possible diluents for carrying out the process according to the invention are inert organic solvents.

These include, in particular, ethers, such as ethylene glycol dimethyl ether or diethyl ether; ketones, such as acetone or butanone; nitriles, such as acetonitrile or propionitrile; amides, such as dimethylformamide, dimethylacetamide, N-methylformanilide, N-methylpyrrolidone or hexamethylphosphoric acid triamide, or alcohols, such as methanol, ethanol or propanol.

The reaction temperatures can be varied within a substantial range in carrying out the process according to the invention. The reaction is in general carried out at temperatures between 0° C. and 100° C., preferably at temperatures between 10° C. and 80° C.

For carrying out the process according to the invention, equimolar amounts of saccharine are employed per mol of substituted hydroxylpropylamine of the formula (II). The two reaction partners are dissolved in a suitable solvent at the suitable reaction temperature and the solvent is then removed by distillation in vacuo. The salts thus obtainable are purified with the aid of customary purification methods, for example by recrystallization or reprecipitation. The occasionally amorphous salts are characterized with the aid of spectroscopic methods (IR; $^1$H-NMR).

The active compounds according to the invention exhibit a powerful action against pests and can be used in practice for combating undesirable harmful organisms.

The acitve compounds are suitable for use as agents for combating pests, above all as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum;* Phytophthora species, such as, for example, *Phytophthora infestans;* Pseudoperonspora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compound according to the invention can thereby be used with paraticularly good success for combating cereal diseases, such as, for example, against the causative organism powdery mildew of barley (*Erysiphe graminis*), or for combating rice diseases, such as, for example, against the rice spot disease causative organism (*Pyricularia oryzae*), or for combating vegetable diseases, such as, for example, against the cucumber mildew causative organism (*Sphaerotheca fuliginea*). It should be emphasized that the active compounds according to the invention also have systemic properties, in addition to a good protective activity.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in ULV cold mist and warm mist formulations.

These formulations are produced in known manner, for example by mixing the active compounds with extenders, that is, liquid solvents, liquefied gases under pressure, and/or solid carriers, optionally with the use of surface-active agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cylcohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules or inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultralow volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

In the treatment of soil, active compound concentrations of 0.00001 to 0.1% by weight, preferably 0.0001 to 0.02% by weight, are required at the place of action.

PREPARATION EXAMPLES

Example 1:

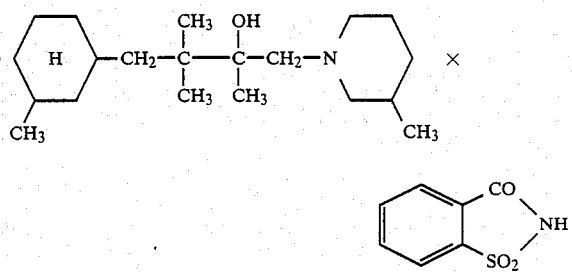

0.7 g (0.00385 mol) of saccharine is added to 1.2 g (0.0039 mol) of 4-(3-methylcyclohexyl)-1-(3-methylpiperidin-1-yl)-2,3,3-trimethyl-butan-2-ol in 40 ml of ethanol and the mixture is stirred at 50° C. for 10 minutes. After the solvent has been removed in vacuo, 1.9 g (100% of theory) of 4-(3-methylcyclohexyl)-1-(3-methylpiperidin-1-yl)-2,3,3-trimethyl-butan-2-ol saccharine salt are obtained as an amorphous solid.

$_1$H-NMR (CDCl$_3$/TMS): $\delta = 3.7$–4.0 (m, 2H); 3.55–3.1 (m, 3H); 2.8 (m, 1H).

Preparation of the starting compounds of the formula (II)

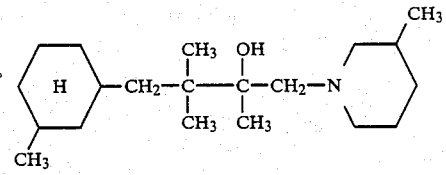

6.8 g (0.022 mol) of 2,3,3-trimethyl-4-(3-methylphenyl)-1-(3-methylpiperidine)-2-butanol are dissolved in 100 ml of isopropanol and hydrogenated with 2 g of 5% strength ruthenium-on-carbon at 130° C. under 200 atmospheres in the course of 4 hours. The catalyst is filtered off and the solvent is distilled off under a water pump vacuum.

6.7 g (99% of theory) of 2,3,3-trimethyl-4-(3-methylcyclohexyl)-1-(3-methylpiperidin-1-yl)-2-butanol of refractive index $n_D^{20}$: 1.4886 are obtained.

The structure is confirmed by the NMR spectra and the purity is confirmed by gas chromatography.

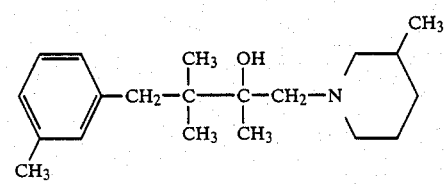

14 g (0.069 mol) of crude 2,3,3-trimethyl-4-(3-methylphenyl)-but-1-ene oxide in 10 ml of n-butanol are added dropwise to 6.9 g (0.07 mol) of 3-methylpiperidine in 40 ml of n-butanol and 0.2 ml of glacial acetic acid and the mixture is heated under reflux for 18 hours. The solvent is then distilled off under a water pump vacuum. The residue is chromatographed over a silica gel column with the eluting agents methylene chloride and methylene chloride/methanol (9:1) in succession.

13.6 g (65% of theory) of 2,3,3-trimethyl-4-(3-methylphenyl)-1-(3-methylpiperidin-1-yl)-2-butanol are obtained as an oil with the refractive index $n_D^{20}$ of 1.5134.

The structure is confirmed by the NMR spectra and the purity is confirmed by gas chromatography.

Preparation of the precursors of the formula (III)

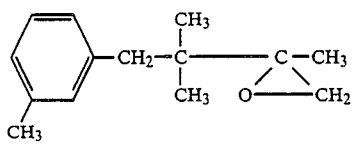

96 g (0.5 mol) of 2,2-dimethyl-1-(3-methylphenyl)-butan-3-one are dissolved in 630 ml of tetrahydrofuran. This solution is added dropwise to a suspension of 132.8 g (0.6 mol) of trimethylsulphoxonium iodide and 68 g (0.6 mol) of potassium tert.-butylate in 160 ml of dimethylsulphoxide, which has first been stirred at 60° C. for 6 hours. The internal temperature increases to 27° C. and the mixture is subsequently stirred at 45° C. for 15 hours. The mixture is then poured onto 2 l of ice-water and extracted 4 times with 500 ml of methylene chloride each time and twice with 500 ml of water. The organic phase is dried and the solvent is distilled off in vacuo.

97.3 g of the crude 2,3,3-trimethyl-4-(3-methylphenyl)-but-1-ene oxide are obtained.

Preparation of the precursors of the formula (V)

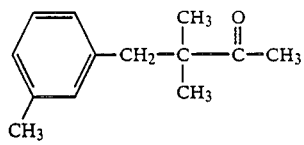

161 g (3 mols) of potassium hydroxide are introduced into 1.25 l of cyclohexane with 24.4 g (0.075 mol) of tetrabutylammonium bromide, and a solution of 258 g (3 mols) of methyl isopropyl ketone and 210 g (1.511 mols) of 3-methylbenzyl chloride is added under reflux. The mixture is then heated under reflux over a water separator for 30 hours and filtered off with suction over kieselguhr, and the filtrate is distilled in vacuo.

100 g (35% of theory) of 2,2-dimethyl-1-(3-methylphenyl)-butan-3-one of boiling point 52° C./0.15 mbar are thus obtained.

The following saccharine salts of substituted hydroxypropylamines of the general formula (I) are obtained in a corresponding manner and in accordance with the general statements on the preparation:

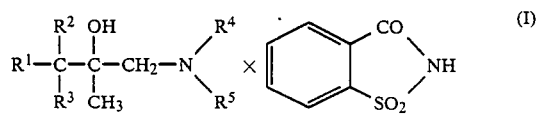

TABLE

| Ex. No. | $R^1$ | $R^2$ | $R^3$ | $-N\begin{smallmatrix}R^4\\R^5\end{smallmatrix}$ | Physical constant |
|---|---|---|---|---|---|
| 2 | 3-Cl-phenyl | CH₃ | CH₃ | piperidinyl | m.p. 150–151° C. |
| 3 | 3-Cl-phenyl | CH₃ | CH₃ | morpholinyl | m.p. 174–175° C. |
| 4 | 3-Cl-phenyl | CH₃ | CH₃ | 3-methylpiperidinyl | m.p. 111–113° C. |
| 5 | 3-Cl-phenyl | CH₃ | CH₃ | 3,5-dimethylpiperidinyl | m.p. 108–110° C. |

TABLE-continued

| Ex. No. | R¹ | R² | R³ | $-N\begin{smallmatrix}R^4\\R^5\end{smallmatrix}$ | Physical constant |
|---|---|---|---|---|---|
| 6 | 3-Cl-C₆H₄- | CH₃ | CH₃ | 2,6-dimethylmorpholino | m.p. 94-99° C. |
| 7 | 3-Cl-C₆H₄- | CH₃ | CH₃ | hexahydro-1H-azepin-1-yl | m.p. 147-150° C. |
| 8 | 4-(CH₃)₃C-C₆H₄- | CH₃ | CH₃ | 2,6-dimethylmorpholino | ¹H—NMR*:<br>4.5-4.1<br>3.7-3.6<br>3.4-3.3 |
| 9 | 4-(CH₃)₃C-C₆H₄- | CH₃ | CH₃ | 3,5-dimethylpiperidino | ¹H—NMR*:<br>3.5-2.5 |
| 10 | 4-(CH₃)₃C-C₆H₄- | CH₃ | CH₃ | morpholino | ¹H—NMR*:<br>4.2-3.55<br>3.7-3.2<br>0.85 |
| 11 | 4-(CH₃)₃C-C₆H₄- | CH₃ | CH₃ | piperidino | ¹H—NMR*:<br>3.95-3.7<br>3.35<br>3.2-3.0 |
| 12 | 4-(CH₃)₃C-C₆H₄- | H | CH₃ | 3,5-dimethylpiperidino | ¹H—NMR*:<br>1.0 |
| 13 | 3-Cl-2-CH₃-C₆H₃-O-CH₂- | CH₃ | CH₃ | 2,6-dimethylmorpholino | mp. 114°-120° C. (decomp.) |
| 14 | 3-CH₃-C₆H₄-CH₂- | CH₃ | CH₃ | 2,6-dimethylmorpholino | mp. 72°-78° C. |

TABLE-continued

| Ex. No. | R¹ | R² | R³ | −N(R⁴)(R⁵) | Physical constant |
|---|---|---|---|---|---|
| 15 | 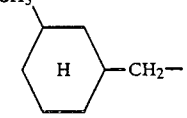 CH₃-cyclohexyl-CH₂− | CH₃ | CH₃ | 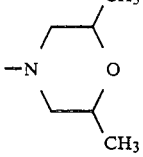 morpholine with two CH₃ groups | mp. 75°–85° C. |

*The ¹H—NMR spectra were recorded in CDCl₃ with tetramethylsilane (TMS) as the internal standard. The chemical shift as the δ value in ppm is given.

USE EXAMPLES

The compounds shown below were employed as comparison substances in the use examples which follow:

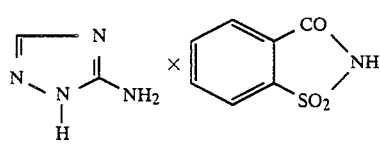

(A)

5-Amino-1,2,4-triazole saccharine salt and

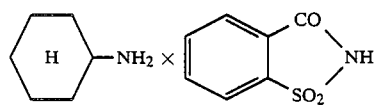

(B)

Cyclohexylamine saccharine salt (both known from European Pat. No. 158,074) and

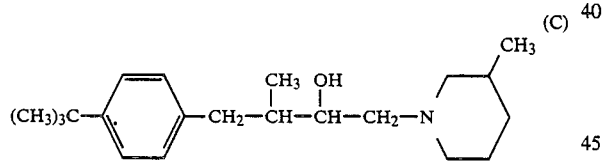

(C)

4-(4-t-butylphenyl)-3-methyl-1-(3-methyl-piperidin-1-yl)-butan-2-ol (known from European Pat. No. 129,321)

EXAMPLE A

Erysiphe test (barley)/protective

Solvent: 100 parts by weight of dimethylformamide
Eulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the preparation Examples 2, 3, 4, 5, 6, 7, 12.

EXAMPLE B

Pyricularia test (rice)/protective

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for Example, by the compounds according to the preparation examples 5, 6, 9 and 10.

EXAMPLE C

Pyricularia test (rice)/systemic

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the preparation Examples 5, 6, 9, 10 and 12.

It will be understood that the specification and examples are illustrative but not limitative of the present invention and that other embodiments within the spirit and scope of the invention will suggest themselves to those skilled in the art.

What is claimed is:

1. A saccharine salt of a substituted hydroxypropylamine of the formula

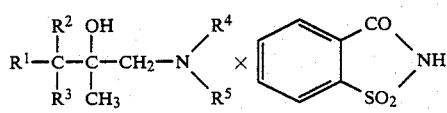

in which
R$^1$ is benzyl or monolower alkyl benzyl,
R$^2$ is hydrogen or methyl,
R$^3$ is methyl or ethyl, and
R$^4$ and R$^5$, together with the nitrogen atom to which they are bonded, form a morpholine radical which is optionally substituted once or twice by lower alkyl.

2. A saccharine salt according to claim 1, wherein such salt is 4-(3-methylphenyl)-1-(2,6-dimethyl-morpholin-4-yl)-2,3,3-trimethyl-butan-2-ol saccharine salt of the formula

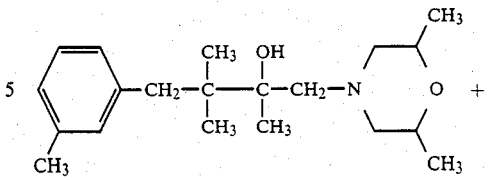

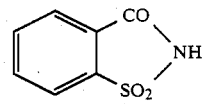

3. A saccharine salt according to claim 1, wherein such salt is 4-(4-t-butylphenyl)-1-(morpholin-4-yl)-2,3,3-trimethyl-butan-2-ol saccharine salt of the formula

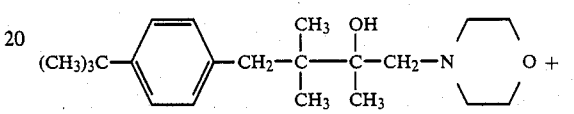

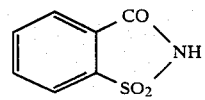

4. A fungicidal composition comprising a fungicidally effective amount of a saccharine salt according to claim 1 and a diluent.

5. A method of combating fungi which comprises applying to such fungi or to a fungus habitat a fungicidally effective amount of a saccharine salt according to claim 1.

6. The method according to claim 5, wherein such salt is
4-(3-methylphenyl)-1-(2,6-dimethyl-morpholin-4-yl)-2,3,3-trimethyl-butan-2-ol saccharine salt, or
4-(4-t-butylphenyl)-1-(morpholin-4-yl)-2,3,3-trimethyl-butan-2-ol saccharine salt.

* * * * *